United States Patent [19]

Levine

[11] 4,048,343
[45] * Sept. 13, 1977

[54] METHOXYMETHANE STERILIZATION METHOD

[75] Inventor: Irving E. Levine, Mill Valley, Calif.

[73] Assignee: Chevron Research Company, San Francisco, Calif.

[*] Notice: The portion of the term of this patent subsequent to Aug. 19, 1992, has been disclaimed.

[21] Appl. No.: 657,119

[22] Filed: Feb. 11, 1976

Related U.S. Application Data

[60] Division of Ser. No. 504,130, Sept. 9, 1974, abandoned, which is a division of Ser. No. 387,869, Aug. 13, 1973, abandoned, which is a division of Ser. No. 337,519, March 2, 1973, Pat. No. 3,795,750, which is a continuation-in-part of Ser. No. 65,695, Aug. 20, 1970, abandoned, and Ser. No. 238,601, March 27, 1972, abandoned, said Ser. No. 236,601, is a continuation-in-part of Ser. No. 163,532, July 8, 1971, abandoned, which is a continuation-in-part of Ser. No. 65,695.

[51] Int. Cl.$^2$ .......................... A23C 3/00; A23L 3/00
[52] U.S. Cl. .................................. 426/330.2; 21/58; 426/330.3; 426/332; 426/335; 426/422
[58] Field of Search ............... 426/320, 332, 317, 310, 426/442, 429, 321, 473, 474, 475, 422, 424, 426, 430, 436, 472, 330, 330.5, 330.2, 330.3, 330.4, 335, 323; 21/58; 260/428.5; 424/339, 342

[56] References Cited

U.S. PATENT DOCUMENTS

| 128,371 | 6/1872 | Dotch | 424/342 |
|---|---|---|---|
| 950,950 | 1/1906 | Oehme | 426/429 X |
| 1,974,542 | 9/1934 | Parkhurst et al. | 260/428.5 |
| 2,712,698 | 7/1955 | Webb | 426/472 X |
| 2,859,117 | 11/1958 | Braus et al. | 426/429 X |
| 3,900,288 | 8/1975 | Levine | 426/320 |

OTHER PUBLICATIONS

Gammon et al., "Gaseous Sterilization of Foods"; AICHE 345 E. 47 St., N.Y., N.Y. 10017; Seventy Fifth National Meeting, June 6, 1973, Det. Michigan; Col. 1-27 and Graphs.

*Primary Examiner*—S. Leon Bashore
*Assistant Examiner*—Kenneth M. Schor
*Attorney, Agent, or Firm*—D. A. Newell; John Stoner, Jr.

[57] ABSTRACT

Sterilization is accomplished by contacting microorganisms with methoxymethane. Foodstuffs are also defatted and/or dehydrated by solvent extraction with methoxymethane, or dimethyl ether, as it is also called.

5 Claims, No Drawings

METHOXYMETHANE STERILIZATION METHOD

CROSS-REFERENCE TO RELATED APPLICATIONS

This application is a continuation of copending application Serial No. 504,130, filed Sept. 9, 1974, now abandoned which is a division of application Ser. No. 387,869, filed Aug. 3, 1973, which, in turn, is a division of application Ser. No. 337,519, filed Mar. 2, 1973, now U.S. Pat. 3,795,750, which, in turn, is a continuation-in-part of copending application Ser. No. 65,695, filed Aug. 20, 1970, now abandoned, and copending application Ser. No. 238,601, filed Mar. 27, 1972 now abandoned. The aforesaid application Ser. No. 238,601 is a continuation-in-part of copending application Ser. No. 163,532, filed July 8, 1971, now abandoned which, in turn, is a continuation-in-part of application Ser. No. 65,695, filed Aug. 20, 1970. The aforesaid application Ser. No. 387,869 is now abandoned following the filing of continuation application Ser. No. 510,201 on Sept. 30, 1974, which issued Aug. 19, 1975 as U.S. Pat. No. 3,900,288.

BACKGROUND OF THE INVENTION

This invention relates to sterilization with methoxymethane. More particularly, the invention concerns the sterilization of areas or articles contaminated by microorganisms, including foods and beverages, by contacting them with methoxymethane.

Sterilization of areas or materials ordinarily involves the application of stringent measures such as heating, adding chemical preservatives, chemical treating, or radiation. These stringent measures have substantial drawbacks, especially so far as foods and beverages are concerned. Sterilizing with heat requires elevated temperatures which are impractical for general application involving wide areas or large materials, and the heating also may cause undesirable alterations in the flavor and texture of the material sterilized, as in the case of foods and beverages. Chemical additives leave a residue and may change the appearance and taste of the sterilized material, as chemical treatment may also, as in the case of sulfur dioxide treatment of food such as raisins and dried prunes and beverages such as wines. Radiation causes flavor and texture alterations as well as involving various operating difficulties that make it hazardous to use.

This invention also relates to the extraction of normally solid foodstuffs, such as meat and vegetables, as distinct from liquid, such as milk and fruit juices, with methoxymethane, also called dimethyl ether, to remove water and fat as well as other materials soluble in the dimethyl ether, for example, cholesterol.

As obtained from natural sources, such as from animals, vegetables, fungi, bacteria, or algae, food is mainly composed of four classes of substances. These are protein, fat, carbohydrates, and water. In its natural form, food has a tendency to spoil; some of its ingredients are considered undesirable from a health standpoint; and its often substantial water content not only facilitates spoilage but also contributes undesirable bulk and weight, which makes its transportation more difficult and costly. These problems have been recognized for many years. Foods have been preserved by drying even by primitive peoples. Sterilization and canning are now common practice. More recently, freeze drying has proved to be effective but costly. Within the last century, nonfat dried milk has become a major article of commerce worldwide.

SUMMARY OF THE INVENTION

An improved sterilization method has now been found which comprises contacting microorganisms in an area or article with methoxymethane. After sterilization the area or article sterilized is preferably protected against introduction of microorganisms as, for example, by the use of a protective wrapper, container, or the like.

In particular, substances of the class consisting of foods and beverages are effectively sterilized or preserved by contacting the substances with methoxymethane and protecting the sterility of the substance. Similarly, areas or articles in general are sterilized and protected.

The sterilization or preserving methods of the present invention have many advantages compared to previous techniques. Because of the low boiling point of methoxymethane heat is not required and there are none of the usual undesirable side effects due to the use of elevated temperatures. Also, the relative chemical inertness of the methoxymethane insures against the presence of residues which may change the flavor, texture and/or appearance as would be particularly objectionable in the case of foods and beverages. An improved method of defatting and/or dehydrating normally solid foodstuffs of animal, vegetable or microbial origin, has also now been found which comprises subjecting said foodstuffs to a solvent extraction with liquid dimethyl ether, usually at temperatures below 30° C., and separating the dimethyl ether extractant solution.

The dimethyl ether has unique properties for extracting both water and fats, as well as certain other substances soluble in the dimethyl ether, which make it possible to prepare normally solid foodstuffs, such as meat and vegetables, in a substantially dried and low fat form, in which form the food can be stored for long periods of time without taking special precautions such as sterilization, refrigeration or freezing, or freeze drying. The unique properties of dimethyl ether which make it possible to accomplish these valuable results in a more economical manner than by other known processes are its low boiling point and ease of removal from the extracted food product, thereby eliminating the possibility of trace residues of the extractant; dimethyl ether's low level of taste and odor; its lack of toxicity; its ability to dissolve both water and fatty materials; and, finally, its relative chemical inertness. Dimethyl ether does not form peroxides upon exposure to air in the way that diethyl ether does, for example; nor does it form condensation products in the way acetone does. This lack of chemical reactivity under conditions of use avoids the formation of undesirable flavors and odors.

An added advantage of the present method is the concurrent extraction of water along with the fat. The ability of the process to remove both water and fat is particularly important because in the case of some foodstuffs it seems that water may act to prevent completely effective extraction of the fat, as in the case of extraction with diethyl ether.

The defatted and/or dehydrated foodstuff prepared in accordance with the method of the present invention is conveniently reconstituted to edible form. For example, water may be added as required, and the foodstuff heated or cooked, as by frying, in any of the commonly used edible fats or oils. Optionally, a fat either the same or different from that removed in the extraction may also be added at any desired concentration to give a more completely reconstituted food.

DESCRIPTION OF THE PREFERRED EMBODIMENTS

Methoxymethane or dimethyl ether, as it may also be termed, has the formula $C_2H_6O$. It is a colorless gas and has a slight ethereal odor. It is normally kept as a liquefied gas under its own vapor pressure of 60 pounds per square inch gauge at 70° F. Although methoxymethane is an ether, it is unusual in that it does not form peroxides under normal storage and use conditions.

The methoxymethane can be used as a sterilant in several forms, including pure liquid methoxymethane, solutions in other liquids, such as water, and gaseous methoxymethane. Preferably, gaseous methoxymethane is used in the presence of water vapor for maximum effectiveness.

Any suitable means of contacting microorganisms in an area with methoxymethane may be used. In the treatment of articles or confined areas of microorganisms such as encountered in the processing of foods and beverages, the microorganisms are suitably contacted with methoxymethane under pressure, usually in liquid form. Methoxymethane solutions are thereby formed with liquids normally present in the foods and beverages. In many instances the article sterilized may be contacted with liquid methoxymethane, which is then allowed to evaporate, thus providing both liquid and gas contacting of the microorganisms. In the treatment of large areas such as pressure chambers and the like, methoxymethane gas under pressure is conveniently employed.

In the sterilization of foods and beverages the typical microorganisms are most effectively controlled by contacting with methoxymethane at pressures sufficient to maintain liquid state, usually in the range of from about 30 to about 75 pounds per square inch or higher. Contact times adequate to kill the microorganisms are used, ordinarily ranging from as brief as one minute to as long as one hour or more. Although a particular advantage of sterilization with methoxymethane lies in its effectiveness at ambient or room temperatures, either lower or higher temperatures may be employed as desired as, for example, to maintain liquid contact or to evaporate dissolved methoxymethane.

Any concentration of the methoxymethane may be used so long as it is an effective amount sufficient to reduce the microorganisms in the contacted area. The concentration of methoxymethane may be varied depending on the pressure, time, and temperature conditions. In the case of the sterilization of liquids sufficient methoxymethane to provide a partial pressure of about 10 pounds per square inch is desirable for effective sterilization.

The microorganism contacted by the methoxymethane in accordance with the procedure of the present invention may be any bacteria or protozoa. In the case of foods and beverages certain particular organisms are effectively controlled. Examples include in milk processing *Lactobacillus bulgaricus, Streptococcus cremoris, Escherichia coli, Clostridium perfringens*, and *Staphylococcus aureus*; in food processing *Staphylococcus aureus* and *Salmonella typhimurium*.

Following the sterilization, removal of methoxymethane as desired is readily achieved by venting the sterilized area to the atmosphere. Because of the low boiling point of methoxymethane very little residue remains after evaporation under normal conditions. In the case of sterilization of liquids such as beverages where the methoxymethane may be in solution, stripping is effectively accomplished, either by applying a vacuum, sparging with an inert gas, or by raising the temperature if necessary. In many of the sterilization procedures adaptable to closed systems the methoxymethane is recovered following its separation and is available for recycling for further use.

After the microorganisms of an area are contacted and sterilized or effectively controlled, it is desirable in most cases to protect the sterilized area against introduction of other microorganisms. In the case of foods and beverages containers such as cans and bottles customarily provide such protection. Other enclosure means such as wrapping with films and the like may also be useful.

The dimethyl ether extraction of foodstuffs in accordance with the method of the present invention is relatively straightforward and involves little in the way of complex procedures or equipment. The extraction is carried out by bringing the dimethyl ether into intimate contact with the foodstuff and separating the dimethyl ether extractant solution containing the extracted fat and/or water from the insoluble residue. The dimethyl ether is in liquid form as it is brought into contact with the foodstuff, remains in the liquid form throughout the process, and is separated in the liquid form. Following separation, any residual dimethyl ether traces in the foodstuff readily evaporate at ordinary pressures and temperatures, although elevated temperatures or vacuums are not precluded.

It is desirable to have the foodstuff in some comminute form prior to the dimethyl ether extraction in order to ensure proper contacting of the fat and/or water to be extracted. For this purpose the foodstuff may be ground as, for example, by putting meat through a grinder. In like manner vegetables may be ground or they may be shredded in order to preserve desirable texture. In some cases foodstuffs may be cut into thin slices or small cubes or other shapes of appropriate dimensions sufficient to give effective extraction. The comminuting may be carried out in the presence of dimethyl ether and the two operations accomplished at one time.

The comminuted foodstuffs are subjected to the extraction by contacting with the dimethyl ether, as already mentioned. The extraction may be effected by mixing the foodstuff and the dimethyl ether together. Shaking or stirring of the mixture is usually desirable to improve the efficiency of the extractive operation. Although the solvent extraction is conveniently carried out on a batch basis, it is also possible to employ a continuous process. For example, the foodstuffs and the dimethyl ether may be fed into a contacting zone and the dimethyl ether extractant solution and the extracted foodstuff continuously withdrawn in separate streams. Countercurrent extraction processes in which the foodstuff and the dimethyl ether are circulated in the contact zone in counterflow to one another may be used.

After the foodstuff and the dimethyl ether have been contacted sufficiently to provide the desired extraction, the extractant solution and the foodstuff are separated by conventional procedures. In a particular method the foodstuff and the dimethyl ether mixture is allowed to separate by gravity and the dimethyl ether extractant solution is withdrawn in liquid form. Other means of separation such as decanting, centrifugation and filtering may also be used provided that the dimethyl ether extractant solution is maintained in liquid form. The dimethyl ether extractant solution is easily separable, usually by distillation. The dimethyl ether is readily recoverable for recycling to the process or other use. The steps of extraction and separation may be repeated as often as necessary to obtain a residue having the desired fat and water concentration. Usually a number of stages of from 1 to 50 and higher is satisfactory for a batch process.

Although the extraction method of the present invention has several advantages in that no complicated heating and pressuring procedures are required, it is necessary that the dimethyl ether be in substantially liquid form in order to provide proper contact with the fat and/or water to be extracted from the foodstuff. Since most of the fat and water would be left in the residue if the dimethyl ether is withdrawn by evaporation, it is necessary that the dimethyl ether extractant solution be separated in liquid form. Suitable temperatures and pressures are readily maintainable to keep the dimethyl ether in substantially liquid form.

The extraction of foodstuffs by contacting with dimethyl ether in accordance with the method of this invention is carried out usually without heating. Desirably the process permits the use of moderate and lower temperatures which do not adversely affect the flavor and texture of the foodstuff. In the preferred embodiment of the process the solvent extraction is carried out at temperatures below about 30° C. Although the pressures employed during the process may vary, it is preferred that they be sufficient to maintain the dimethyl ether in substantially liquid form. Autogenous pressures are generally sufficient for this purpose.

Examples of foodstuffs which are effectively treated in accordance with the method of this invention include meat of all kinds, fish, poultry, eggs, milk solids, cheese, vegetables such as beans, rice, nuts and potatoes, any of which may be either cooked or uncooked.

Following the defatting and dehydrating of the foodstuff by the method of the invention, some further processing may be desired. For example, the extracted foodstuff may be heated or irradiated as desired to deactivate enzymatic materials which can catalyze further change in the extracted foodstuff. Also other materials may be added to the extracted foodstuff such as food colors and antioxidants. As an illustration, small amounts (about 0.01%) of the FDA-approved commercial antioxidant butylated hydroxytoluene, known as BHT, may be employed to prevent undesirable oxidizing deterioration.

The following examples are further illustrative of the improved method of concurrently defatting and dehydrating foodstuffs of natural origin in accordance with this invention, as well as the foodstuffs derived therefrom. Unless otherwise specified, the proportions in the illustrative examples are on a weight basis.

EXAMPLE 1 -One Step Extraction

A Fischer-Porter bottle having a volume of 300 ml was charged with 70 grams of ground beef. The bottle was then connected to a valve assembly, and 135 grams of dimethyl ether was added. The valve was closed, and the bottle was shaken at 48 cycles/min. for 10 minutes. At the end of this time, the liquid phase was separated from the solid meat phase by filtration and removed. The dimethyl ether extract was analyzed and found to contain 7.9 grams of water and 2.8 grams of fat. The meat used for this experiment contained 6.5 grams of fat and 45.9 grams of water. Therefore a single extraction using about a 2:1 weight ratio of ether:meat removed 44% of the fat and 17% of the water.

EXAMPLE 2 -Six Step Extraction

Using the apparatus and procedure of Example 1, 100 parts of ground beef was extracted with six separate but approximately equal portions of dimethyl ether totaling 1285 parts. All ether extracts were combined and analyzed for 53.3 parts of water and for 27.3 parts of fat.

The extracted meat was placed in a funnel through which was passed a stream of nitrogen for one-half hour to remove the last traces of dimethyl ether. The insoluble residue resulting from this treatment weighted 19.4 parts. It was analyzed for water and for fat by methods 23.003, 23.005, and 22.033 appearing in the "Official Methods of Analysis" of the Association of Official Agricultural Chemists, 10th ed. published in 1965. This analysis showed 0.3 parts of fat and 1.9 parts of moisture remaining. The original meat contained 27.6 parts of fat and 55.2 parts of water. Therefore, a six stage extraction removed 99% of the fat and 97% of the water.

EXAMPLE 3 -Extraction with Isopropyl Alcohol

A portion of ground beef from the same source as in Example 2, 100 parts, was extracted with six separate but approximately equal portions of isopropyl alcohol totaling 1346 parts of water and 15.4 parts of fat. Thus, under conditions comparable with those of Example 2, an isopropyl alcohol extraction removed only 56% of the fat and 99+% of the water.

The insoluble extracted meat residue required drying in a vacuum oven at 40° C under 200 mm of pressure for 36-48 hours for the removal of all traces of isopropyl alcohol.

This example illustrates that although isopropyl alcohol is an excellent dehydrating solvent it is very much inferior to dimethyl ether in defatting. Furthermore, the example shows that long term heating under vacuum is necessary to completely remove the isopropyl alcohol solvent. By contrast, a period of only one-half hour at ambient temperature and pressure is satisfactory for the removal of dimethyl ether.

EXAMPLE 4 -Two Solvent Extraction

Using the apparatus and procedure of Example 1, 70 grams of ground beef was extracted with three approximately equal portions of isopropyl alcohol totaling 465 grams. The three extracts were combined and analyzed for 38.4 grams of water and 1.14 grams of fat. Then the meat was extracted with three approximately equal portions of dimethyl ether totaling 451 grams. These three extracts contained 12.1 grams of water and 2.9 grams of fat. The total water removed was 50.5 grams and the total fat removed was 4.05 grams.

The insoluble residue was dried and analyzed as in Example 2. This residue weighed 15.4 grams and contained 0.76 gram of water and 0.14 gram of fat. Thus, the extraction, first by isopropyl alcohol and then by dimethyl ether, removed 99% of the moisture and 97% of the fat.

EXAMPLE 5 -Extraction with Diethyl Ether

Ground beef was analyzed and found to contain 68.5% water and 8.8% fat. This meat, 70 grams, was extracted by the method of Example 2 using six separate but approximately equal portions of diethyl ether totaling 900 grams. The ether extracts were combined and found to contain 11.5 grams of water and 4.8 grams of fat. Thus, a six-stage extraction procedure utilizing diethyl ether as the solvent removed only 24% of the water and 77% of fat. Under same conditions, dimethyl ether typically simultaneously removes over 90% of both the fat and water from treated foodstuffs.

The insoluble residue required drying for 1-1/2 hours at 40° C in order to remove all traces of the ethyl ether solvent.

This example shows that in the presence of moisture, diethyl ether is not a good extractive solvent for either fat or water. This example also demonstrates that it is more difficult to remove diethyl ether from the extracted residue than it is to remove dimethyl ether.

EXAMPLES 6 through 8 -Extractions of Other Foodstuffs

The following examples were carried out using the apparatus, procedure and analytical methods of Example 2.

| Example No. | Proteinaceous Material Type | Grams | Dimethyl Ether Grams | Insoluble Residue H₂O % | Percent Extracted Water | Fat |
|---|---|---|---|---|---|---|
| 6 | Ground chicken breast | 107.2 | 1060 | 22.3 | 91 | 91 |
| 7 | Ground salmon filet | 63.1 | 1036 | 23.0 | 96 | 96 |
| 8 | Fresh egg, whole | 57.9 | 835 | 16.7 | 98 | 98 |

EXAMPLE 9 -Reconstitution of Extracted Foodstuff

The product of Example 2, 15 grams, was mixed with about 59 grams of water and formed into a patty. This patty was fried with peanut oil sufficient to prevent sticking in a skillet. The cooked product compared to freeze dried cooked hamburger was more edible and had more desirable taste as determined by a panel of four persons.

EXAMPLE 10 -Storage Stability

A sample of meat residue prepared as in Example 2 was stored in a screw-capped jar at ambient temperature for 3 months. At the end of this time, a total bacterial count analysis showed that the stored material contained less than 100 bacteria per gram and no mold at all. Ordinarily, edible fresh ground beef has a bacteria count of about $10^6$ per gram. Thus, this example demonstrates that the present process effectively removes fat and water from a foodstuff and eliminates bacteria and mold. The complete absence of bacteria and mold after 3 months storage shows that the food residue has a substantial shelf-life. The product can, therefore, be easily transported from the producer to the consumer without spoilage and at minimum cost.

The following examples further illustrate the sterilization with methoxymethane in accordance with the present invention. Unless otherwise indicated, percentages are on a weight basis.

EXAMPLE 11 -Sterilization of Milk

A number of experiments were carried out to evaluate methoxymethane as a sterilizing agent for milk and to compare the results of this method of sterilization with thermal sterilization. In each experiment fresh, raw milk was placed in a laboratory pressure bottle. Methoxymethane was then added as a vapor from a pressure cylinder until the pressure in the laboratory bottle reached the desired test pressure. After addition of the methoxymethane the bottle was sealed and shaken for the desired test time in a variable speed laboratory shaker. The pressure was then released and the methoxymethane removed by venting.

For comparative purposes a sample of the same milk was heat sterilized in a sealed laboratory pressure bottle by heating for 20 minutes at 240°-259° F in a laboratory pressure autoclave.

Bacteria counts were run on the milk, both before and after treatment, according to "Standard Methods for the Examination of Dairy Products," 12th ed., American Public Health Association, Inc.

Typical results are given in the following table:

I

| | Standard Plate Count, Cells/ml | Coliform Count, Cells/ml | Pseudomonas Count, Cells/ml |
|---|---|---|---|
| Original Raw Milk | $76 \times 10^4$ | 40 | $45 \times 10^3$ |
| After Methoxymethane Treatment, 60 psig for 1 Hr | <100 | Neg. | Neg. |
| After Thermal Treatment, 240–259° F for 20 Min. | <100 | Neg. | Neg. |

Effect of methoxymethane contact time was determined by treating raw milk with methoxymethane at 60 psig for different time periods using the laboratory procedure outlined above.

TABLE II

| Methoxymethane Contact Time at 60 psig, Minutes | Standard Plate Count, Cells/ml | Coliform Count, Cells/ml | Pseudomonas Count, Cells/ml |
|---|---|---|---|
| Untreated | 1,100,000 | 1 | 230,000 |
| 1 | 3,200 | Neg. | 520 |
| 5 | 4,800 | Neg. | 200 |
| 15 | 200 | Neg. | 20 |
| 25 | <100 | Neg. | <10 |
| 60 | <100 | Neg. | <10 |

Information on the keeping properties at room temperature of methoxymethane-sterilized milk was obtained by treating a sample of raw fresh milk for one hour and 60 psig and then determining the bacteria count after holding for four weeks at 70° F ± 5° F in a closed container.

TABLE III

| | Standard Plate Count, Cells/ml | Coliform Count, Cells/ml | Pseudomonas Count, Cells/ml |
|---|---|---|---|
| Untreated Milk Immediately After Methoxymethane Treatment | $13 \times 10^6$ | 27 | $18 \times 10^4$ |
| | <100 | Neg. | Neg. |
| After One Week at 70° F ± 5° F | <200 | Neg. | Neg. |
| After Two | | | |

TABLE III-continued

| | Standard Plate Count, Cells/ml | Coliform Count, Cells/ml | Pseudomonas Count, Cells/ml |
|---|---|---|---|
| Weeks at 70° F ± 5° F | <100 | Neg. | Neg. |
| After Four Weeks at 70° F ± 5° F | <100 | Neg. | Neg. |

The test results in the above examples show that the methoxymethane is effective in controlling bacteria in milk. Although conditions of time and temperature of contact and concentration are variable depending on the particular micro-organism, it may be seen that a substantial reduction in bacteria is obtained with contact times as short as 5 minutes and pressures of as little as about 30 psig.

Other experiments were carried out to demonstrate the effect of concentration of methoxymethane in the sterilization of milk. A mixture of *Lactobacillus bulgaricus* (a yoghourt organism), *Streptococcus cremoris* (cottage cheese organism), and *Escherichia coli* (member of the human intestinal flora) in nonfat milk were sterilized at 23° C. The exposure time was one hour at pressures of 15, 30 and 58 psi. There was additional time during charging and venting of 0.3 hour at 15 psi, 0.7 hour at 30 psi, and 1 hour at 58 psi. Viable counts were performed on selective media that could distinguish among survivors. Typical results are given in the following table.

TABLE IV

| Organism | Viable Count Before Treatment Cells/ml | Survival After Treatment, % | | |
|---|---|---|---|---|
| | | 15 psi | 30 psi | 58 psi |
| L. bulgaricus | $4.5 \times 10^5$ | 29 | 6.7 | <0.022 |
| S. cremoris | $98 \times 10^6$ | 5.1 | $<10^{-4}$ | $<10^{-4}$ |
| E. coli | $8.6 \times 10^5$ | 5.6 | $<10^{-3}$ | $<10^{-3}$ |

The above test results show that at about 15 psi partial pressure, which is equivalent to about 6% methoxymethane in water, the particular organisms were not killed, but at a partial pressure of 30 psi, equivalent to about 12% in water, two of the three microoganisms were killed. At 58 psi, equivalent to about 24% by weight methoxymethane in water, all three of the microorganisms tested were killed.

EXAMPLE 12 -Sterilization of Grape Juice

Fresh grapes purchased at a local grocery store were crushed in a laboratory grinder. To make sure yeasts were present, the mixture was then inoculated with a small amount of purchased wine yeast culture. A sample of the whole crushed product including juice, pulp, seeds, and skins was placed in a laboratory pressure bottle; and methoxymethane was added as a gas from a pressure cylinder until the pressure in the laboratory bottle reached 60 psig. The bottle was then sealed and shaken for one hour in a variable speed laboratory shaker. The pressure was then released and the methoxymethane removed by venting.

Examination of the crushed grapes for yeasts and molds before and after methoxymethane treatment gave the following results:

TABLE V

| | Yeast, Cells/ml | Mold, Cells/ml |
|---|---|---|
| Before Treatment | 120 | Neg. |
| After Treatment | Neg. | Neg. |

EXAMPLE 13 -Sterilization of Fermenting Wine

A sample of fermenting white wine obtained from a local California winery was placed in a laboratory pressure bottle. Methoxymethane gas was added from a pressure cylinder until the pressure in the bottle reached 62 psig. The bottle was then shaken for one hour under pressure in a variable speed laboratory shaker. At the end of this time, the pressure was released and the methoxymethane vented from the bottle.

Samples of the original wine and the methoxymethane- treated wine were then plated out on grape nutrient agar and incubated at 70° F. After 24 hours there was growth from the original, untreated sample; and the yeast flora was reported as viable. Centrifuged sediment from the original sample was examined microscopically, and the cells observed appeared to be normal.

After 144 hours there was no growth from the methoxymethane-treated sample. Centrifuged sediment from the treated sample was also examined microscopically. The yeast cells observed appeared to have a granulated protoplasm, and there was no evidence of budding.

EXAMPLE 14 -Sterilization of Meat

In a laboratory bottle 100 parts of ground beef was extracted and sterilized by contacting with six separate but approximately equal portions of liquid methoxymethane, totaling 1,285 parts. In the extraction and sterilization the bottle is connected to a valve assembly through which the methoxymethane is added. The valve is closed and the bottle shaken at 48 cycles per minute for 10 minutes. The liquid phase is separated from the solid meat phase by filtration and removed.

The extracted and sterilized meat was placed in a funnel through which was passed a stream of nitrogen for one-half hour to remove the last traces of methoxymethane. The insoluble residue resulting from this treatment weighed 19.4 parts.

A sample of the meat residue obtained above was stored in a screw-capped jar at ambient temperature for three months. At the end of this time a total bacterial count analysis showed that the stored material contained less than 100 bacteria per gram and no mold at all. Ordinarily edible fresh ground beef has a bacteria count of about $10^6$ per gram. Thus this example demonstrates that the present process effectively eliminates bacteria and mold from meat and effectively preserves the food as shown by the complete absence of bacteria and mold after three months' storage.

Tabel VI further illustrates sterilization experiments by giving the results of bacteriological inspection of a number of solid food products kept in closed containers at room temperature after sterilization with methoxymethane using the procedure outlined in Example 14.

TABLE VI

| Food Product | Age, Days | Count/Gram | |
|---|---|---|---|
| | | Total Bacteria | Mold |
| Ground Round Steak | 11 | <100 | Neg. |

TABLE VI-continued

| Food Product | Age, Days | Count/Gram Total Bacteria | Mold |
|---|---|---|---|
| Raw Potatoes | 64 | <100 | Neg. |
| Whole Egg | 66 | <100 | Neg. |
| Ground Salmon Filet | 84 | <100 | Neg. |
| Ground Round Steak | 91 | <100 | Neg. |
| Ground Round Steak | 102 | <100 | Neg. |

Additional experiments were also carried out to demonstrate the methoxymethane sterilization method of the invention employing this sterilizing agent in the gaseous state.

EXAMPLE 15 - Sterilization of Glass Objects

Two silicone rubber rings, 2 cm. in diameter, were mounted on one side of a standard glass microscope slide. The slide was then glued to a polyurethane-rubber sponge saturated with water. This combination was heat sterilized, after which one drop of a *staphylococcus aureus* culture having $88 \times 10^6$ cells/ml. was placed within each ring. The inoculated slide mounted on the moist sponge was then placed in a sterile Fischer-Porter bottle to which there was attached a gas inlet device. The bottle was charged to 60 psig with methoxymethane and held for two hours at ambient temperature. At the end of this time, the bottle was vented. A bacteria count of the slide showed complete sterilization. No germs were found by a test capable of detecting as few as 10 cells/ml.

A comparison slide treated in the same way as described above, except that it was not exposed to methoxymethane, tested for $69 \times 10^6$ and $110 \times 10^6$ cells/ml. at the end of the experiment.

EXAMPLE 16 - Sterilization of Gauze

The procedure of Example 11 was followed, except that an unmedicated gauze "Band-Aid" was pinned to the uretane-rubber sponge. At the end of the test period, the Band-Aid exposed to methoxymethane was sterile (less than 10 cells/ml.); whereas the comparison gauze had a *staphylococcus aureus* count of $114 \times 10^6$ cells/ml.

The results in the above experiments show that methoxymethane is effective in the gaseous state since complete or substantially complete sterilization is obtained, as it was in the previously mentioned experiments demonstrating the effectiveness of methoxymethane in liquid state, either as pure methoxymethane or as aqueous solutions of methoxymethane. It was noted that in both Example 15 and Example 16 the systems had an appreciable moisture content in the form of water vapor as evidenced by some condensation on the inside walls of the Fischer-Porter bottle.

While the character of this invention has been described in detail with numerous examples, this has been done by way of illustration only and without limitation of the invention. It will be apparent to those skilled in the art that modifications and variations of the illustrative examples may be made in the practice of the invention within the scope of the following claims.

I claim:

1. Sterilization or preservation method comprising physically contacting substances of the class consisting of solid foods and beverages contaminated by microorganisms with an effective amount of methoxymethane under pressure and temperature sufficient to maintain the methoxymethane in liquid state and for a contact time with said microorganisms sufficient to effectively control the microorganisms, releasing the pressure and removing methoxymethane by evaporation.

2. The method of claim 1 in which the contacting with methoxymethane is carried out at about room temperature and at pressures of from about 30 to about 75 pounds per square inch.

3. The method of claim 2 in which the substances are solid foods.

4. The method of claim 2 in which the substances are beverages.

5. The method of claim 4 in which the beverage is milk, the methoxymethane is in solution at a partial pressure of at least 30 psi, and the contact time is at least 5 minutes.

* * * * *